United States Patent [19]

Cohen

[11] 4,067,499
[45] Jan. 10, 1978

[54] NON-AEROSOL CONTINUOUS SPRAY DISPENSER

[76] Inventor: Milton J. Cohen, 9201 Persimmon Tree Road, Potomac, Md. 20854

[21] Appl. No.: 658,469

[22] Filed: Feb. 17, 1976

[51] Int. Cl.² .......................................... B05B 9/047
[52] U.S. Cl. .................................... 239/323; 222/95; 222/105
[58] Field of Search ..................... 239/323, 327, 328; 222/183, 319, 386, 95, 105, 182, 215; 128/249

[56] References Cited

U.S. PATENT DOCUMENTS

| 1,235,550 | 8/1917 | Carmody | 239/323 X |
|-----------|--------|---------|-----------|
| 2,649,995 | 8/1953 | Muskin | 222/105 X |
| 3,111,145 | 11/1963 | Kerns | 222/95 X |
| 3,335,913 | 8/1967 | Bouet | 222/95 |
| 3,338,474 | 8/1967 | Olson | 222/95 X |
| 3,838,796 | 10/1974 | Cohen | 222/105 |

Primary Examiner—John J. Love
Assistant Examiner—Michael Mar
Attorney, Agent, or Firm—McDougall, Hersh & Scott

[57] ABSTRACT

A non-aerosol type spray device comprising a container for housing a liquid content material to be dispensed and a plunger slidable as a piston within the container and an elongate tubular member for actuating the plunger with a bore extending continuously therethrough for communication with the interior of the container at one end and communication with a spray nozzle at the other for passage of the liquid content material from the container through the bore to the spray nozzle in response to displacement of the plunger.

2 Claims, 8 Drawing Figures

NON-AEROSOL CONTINUOUS SPRAY DISPENSER

This invention relates to a dispenser for spraying a fluid upon demand, and relates more particularly to a portable hand-operated sprayer which can be used for dispensing different types of fluid compositions such as paints, varnishes, insecticides, herbicides, lubricants, solvents, and the like, and preferably pharmaceuticals, which fluids may be in the form of pure liquids, solutions, emulsions, suspensions, and the like.

To the present, widespread use has been made of fluid dispensers wherein pressure sufficient for spraying is derived from a pressurizing vaporizable fluid of the aerosol type.

Aside from the disrepute to which aerosol dispensers have fallen by reason of release of polluting vapors into the atmosphere, the aerosol spray unit is an expensive item from the standpoint of the cost of parts and materials and the complications which arise in assembly and use. The aerosol container is constantly under a pressurized state whereby danger to personnel exists by reason of the possibility of explosion, and, finally, people have taken to sniffing the aerosol vapors with the result that the possibility exists that such aerosol containers may be banned from the market.

It is an object of this invention to produce a device for spraying liquids which does not make use of an aerosol as a pressurizing means; which does not make use of a propellant that goes off into the atmosphere as a vapor; which does not involve the use of a vaporizable propellant that presents an attraction to children and others as a means for getting "high"; which is capable of substantially complete delivery of the liquid content material to be sprayed; which can be operated for continuous spray as distinguished from the pumping action for intermittent spray characteristic of hand-operated sprayers; which is capable of use as a re-fillable device thereby to minimize the cost and expense characteristic of single-use devices; which is completely pressureless during periods of loading and non-use, thereby to eliminate danger of explosion and thereby to enable the use of less expensive materials which can be easily assembled on a mass-production basis, to provide a low-cost sprayer which offers great flexibility in use.

These and other objects and advantages of the invention will hereinafter appear, and, for purposes of illustration, but not of limitation, embodiments of the invention are shown in the accompanying drawings, in which.

Figure 1:
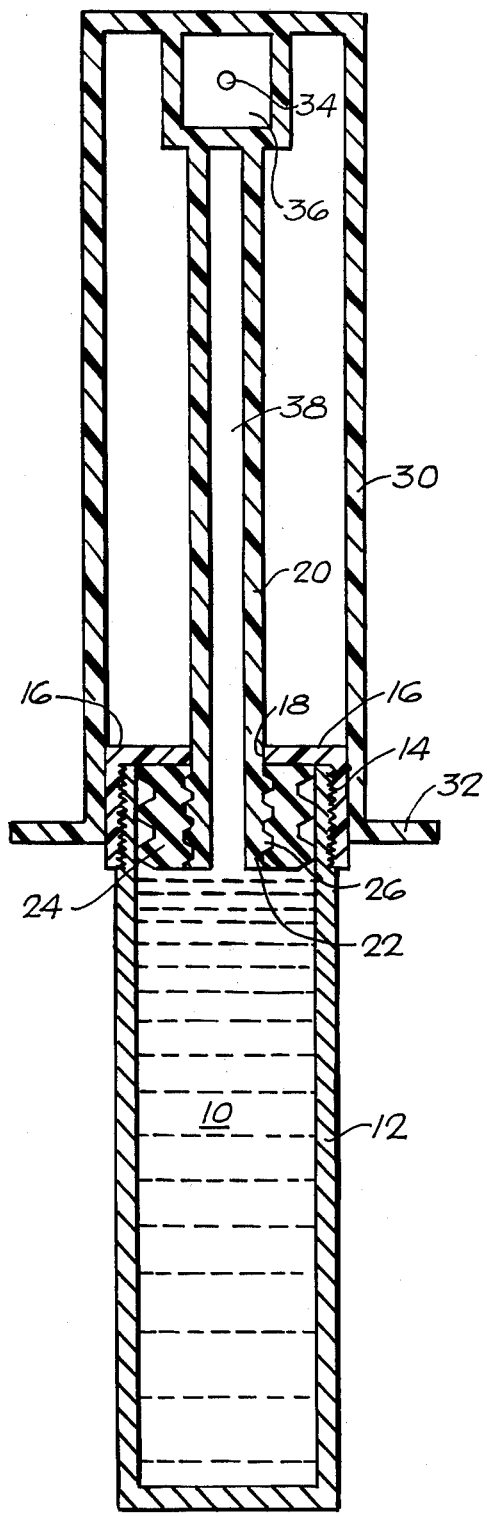
FIG. 1 is a sectional elevational view of a dispenser embodying the features of this invention, showing the elements in non-dispensing state.
Figure 2:
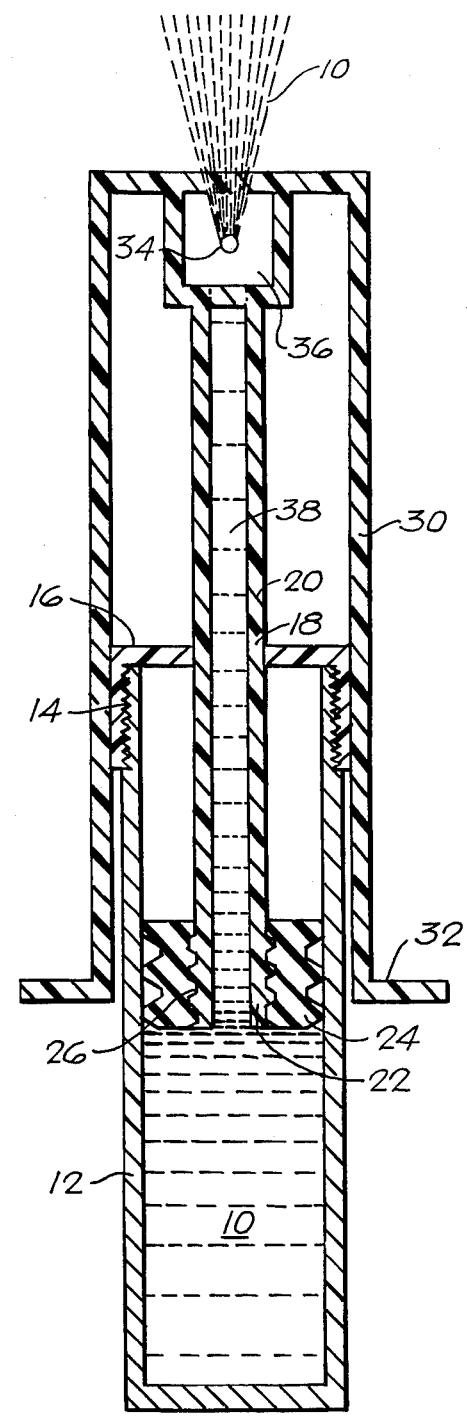
FIG. 2 is a sectional view of the dispenser shown in FIG. 1 showing the relative position of elements during spraying.
Figure 5:
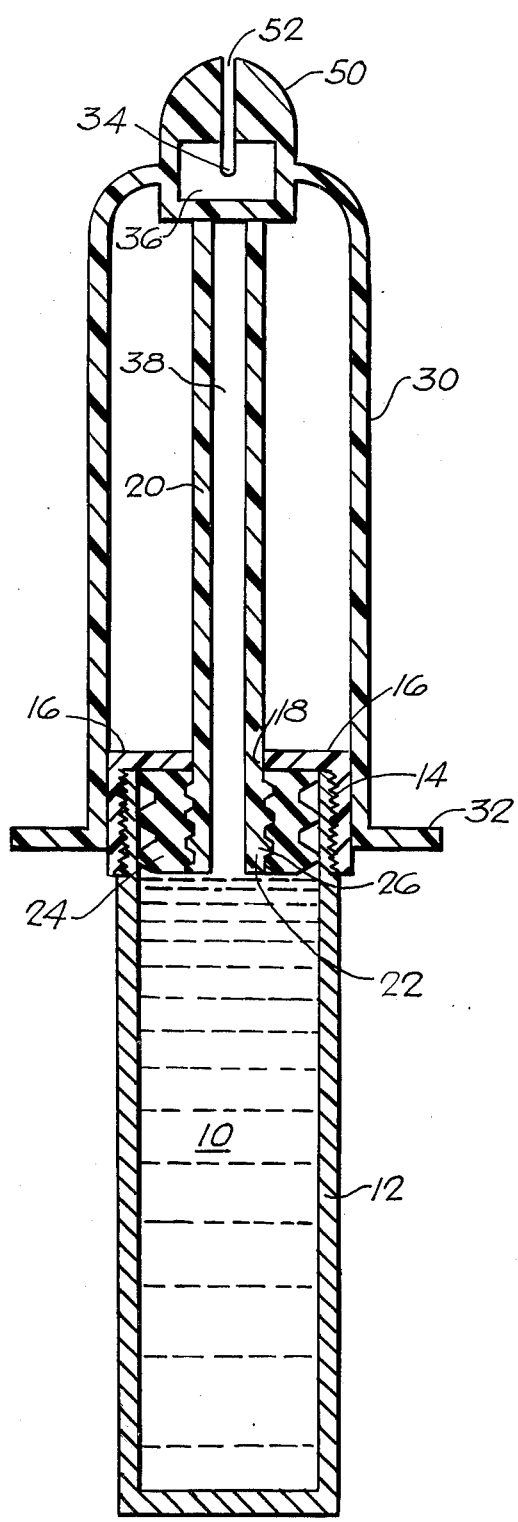
Figure 6:
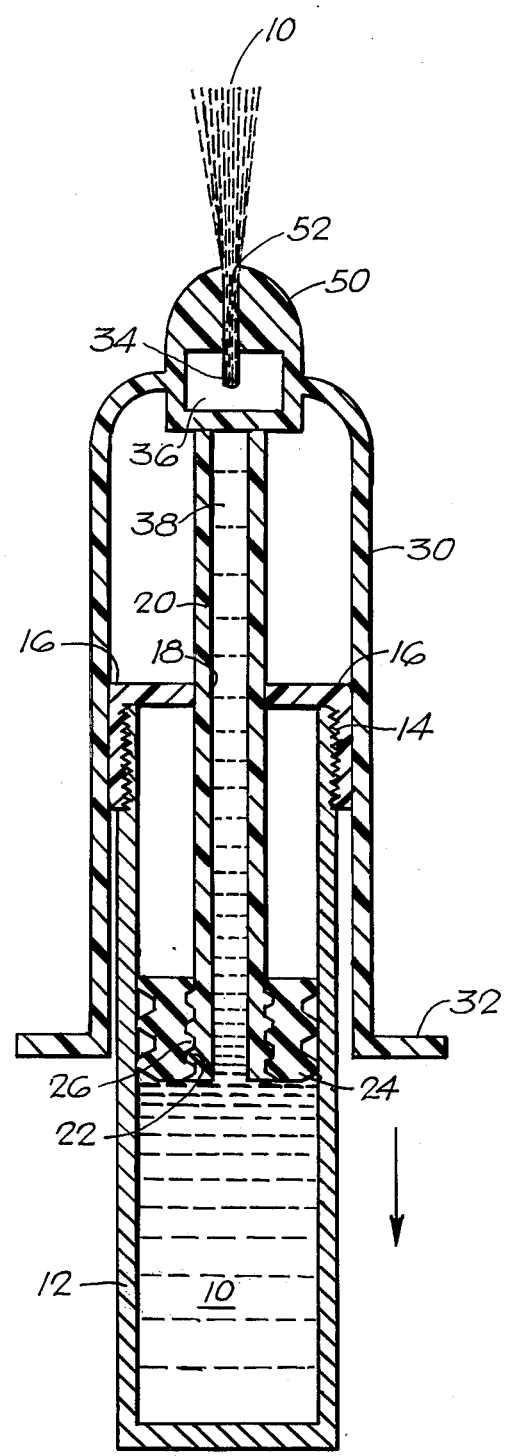
Figure 7:
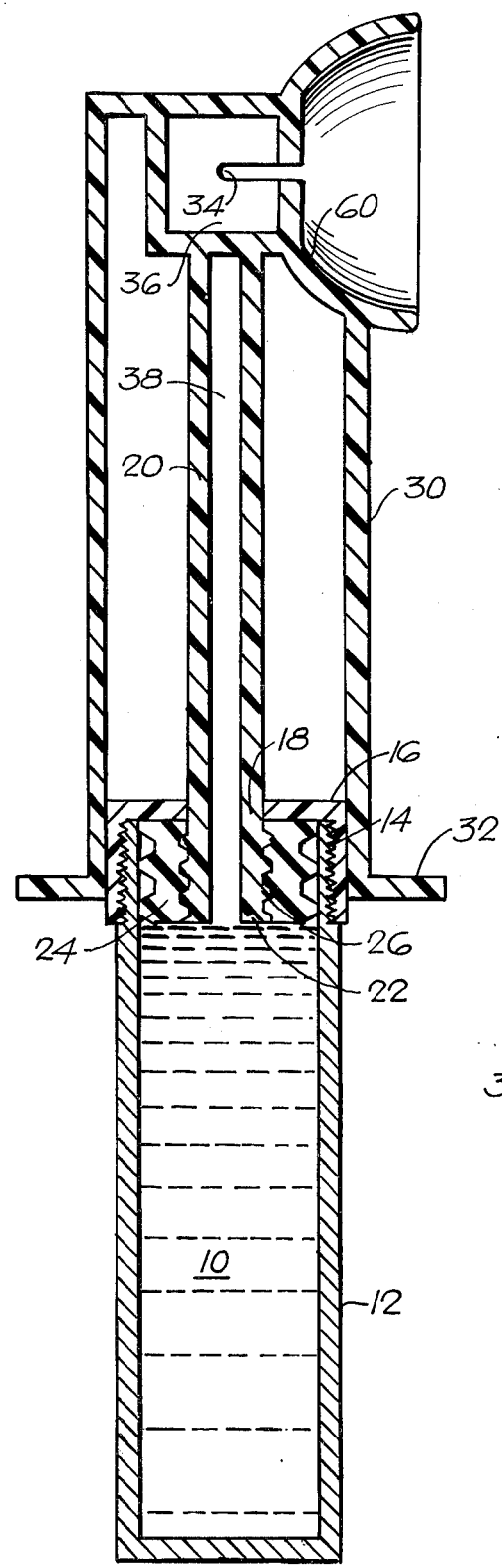
Figure 8:
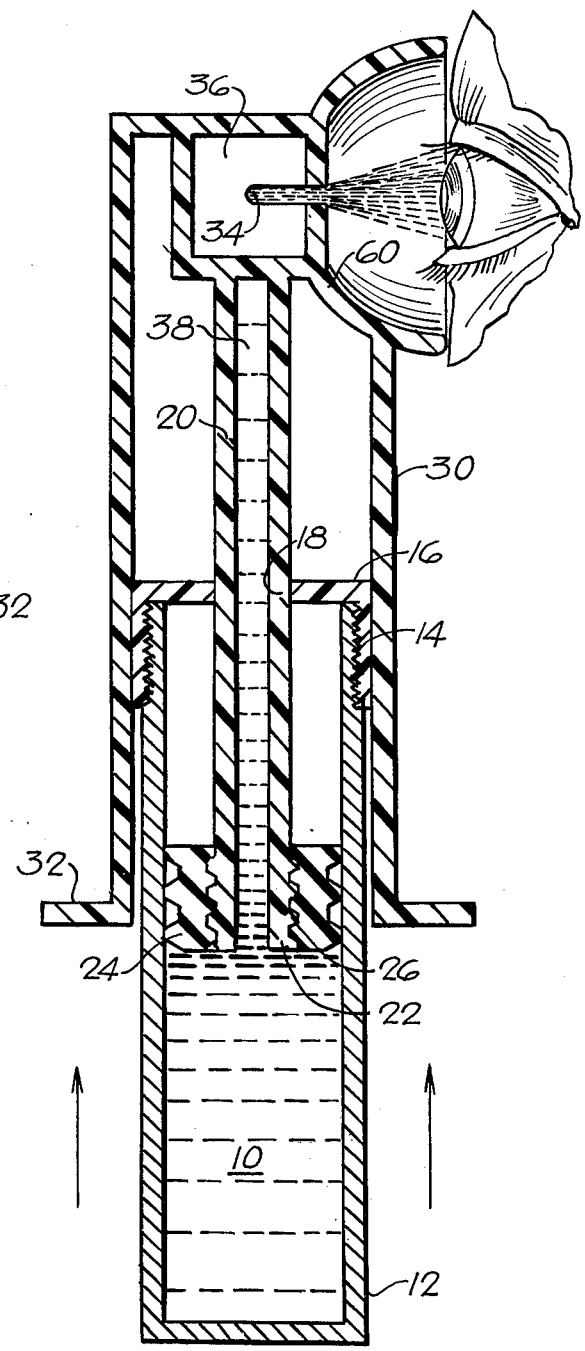

FIGS. 5 and 6 are views similar to those of FIGS. 1 and 2 in which the dispenser is designed for use as a nasal spray; and FIGS. 7 and 8 are views similar to those of FIGS. 1 and 2 in which the dispenser is designed for use as an eye spray.

The basic construction of the sprayer dispenser of this invention is shown in FIGS. 1 and 2 wherein the liquid 10 to be dispensed is confined within a container 12 which is open at one end for access to the interior thereof. The container can be in the form of a bottle, vial, can, or the like formed of clear, translucent, or opaque but relatively rigid, structurally strong material, such as glass, plastics, metal, paper-plastic laminate, or paper-metal laminate and the like, and preferably to cylindrical shape.

The upper end of the container 12 is formed with external screw threads 14 for receiving an internally screw-threaded cap 16 for sealing the open end of the container. An opening 18 is provided through the center of the cap 16 dimensioned to enable an elongate tubular member 20 to extend therethrough in sealing relation to enable sliding movement of the tubular member relative to the closure.

Means are provided on the end portion 22 of the tubular member 20 extending through the opening 18 into the interior of the container for mounting a piston member 24 thereon in the form of a plunger of resilient material dimensioned to engage the inner walls of the container in sliding relation to function in the manner of a piston in a cylinder assembly responsive to relative axial displacement of the piston member through the interior of the container. In the illustrated modification, such means comprises external screw threads 26 on the through-extending portion of the tubular member 20 which threadably engages the internally threaded bore provided in the elastic plunger 24.

The tubular member 20 is dimensioned to have a length at least as great as the lengthwise interior dimension of the container 12 so as to enable the tubular member to effect displacement of the plunger 24 substantially throughout the length of the interior of the container. The tubular member 20 is provided with hand-actuating means for displacement of the plunger to the end of its stroke within the chamber. In the illustrated modification, such means comprises an actuator 30 in the form of an arch which is received in telescoping relation about the container and is provided at its lower ends with outwardly extending flange portions 32 for use as a finger grip. The actuator can be in the form of a cylindrical section having a diameter greater than the outer wall-to-wall diameter of the container or it may comprise a web with the finger grips extending from the opposite arms.

The tubular member is fixed to the actuator for concurrent displacement in the same direction. For this purpose, it is desirable for the actuator to be dimensioned to have a length corresponding to the length of stroke and to be fixed to the tubular member 20 beyond said length.

The end of the tubular member mounts a spray nozzle 34 controlled by a spray valve, indicated by the numeral 36, which communicates with the end of the bore 38 extending continuously through the tubular member. The valve is a conventional pressure-responsive valve which opens in response to pressure liquid content material to permit pressurized liquid to be sprayed from the nozzle.

In use, the container 12 is filled with liquid to be dispensed and the closure 16 with the tubular member 20 extending therethrough is secured by twisting the closure onto the end of the container and the dispenser, illustrated in FIG. 1, is ready for use.

When it is desired to spray liquid content material 10 from the nozzle 34, it is only necessary to grip the container in one hand, with the thumb against the bottom wall of the container and the adjacent fingers looped over the finger grips 32. As one pushes with the thumb and pulls with the fingers, the actuator is displaced in the direction toward the closed end of the container with corresponding movement of the plunger 24. The plunger sweeps the liquid before it so that the liquid becomes pressurized and is forced to flow up through the bore 38 of the tubular member, through the valve, and into the spray nozzle, as illustrated in FIG. 2.

Until the actuator is drawn down relative to the container, the liquid within the container is not under pressure, so that no dispensing will take place. It will also be apparent that the force of the spray can be varied by the pressure applied by hand through the actuator, and that such pressure can be applied for a continuous spray or intermittent spray, all of which is entirely within the control of the user.

In the modification shown in FIGS. 5 and 6, the spray nozzle 34 is built into a parabolic section 50 which extends outwardly from the end of the actuator 30 for receipt in fitting relation in the open end of a nostril. The nose section 50 is formed with the passage 52 extending from the valve through the center of the section for issuing the spray from the end thereof, as illustrated in FIG. 6.

Thus the spray device of the invention can be used with one hand, as a hand-operated nose spray, for continuous or intermittent dispensing of medicaments into the nostril, without introducing extraneous matters, such as propellant gas which might be harmful, and without the danger of harming the delicate tissues of the nose by an otherwise pumping action.

In the modification shown in FIGS. 7 and 8, the spray device is adapted for use in spraying a medicament into the eye by providing the outlet from the spray nozzle 34 in the base of an eye cup 60, in the form of a concave member fixed to form a part of the actuator. In the preferred arrangement, the eye cup is mounted to face in a horizontal direction perpendicular to the length of the container to enable the cup 60 to be held in position about the eye while the actuator is operated to generate the spray of liquid from the container.

It will be apparent that the liquid sprayer, embodying the features of this invention, is capable of being refilled for additional usage thereby to minimize waste and economize on material. For this purpose, it is only necessary to unscrew the closure 16 to enable withdrawal of the plunger and removal of the actuator. This exposes the interior of the container for re-filling from a source of large supply. After the container has been re-loaded, the plunger is reinserted and the cap is screwed down onto the end of the container so that the sprayer is again ready for use.

Valves which open responsive to internal pressure transmitted by the liquid container material are well known and do not need detailed description here.

Figures 3, 4:
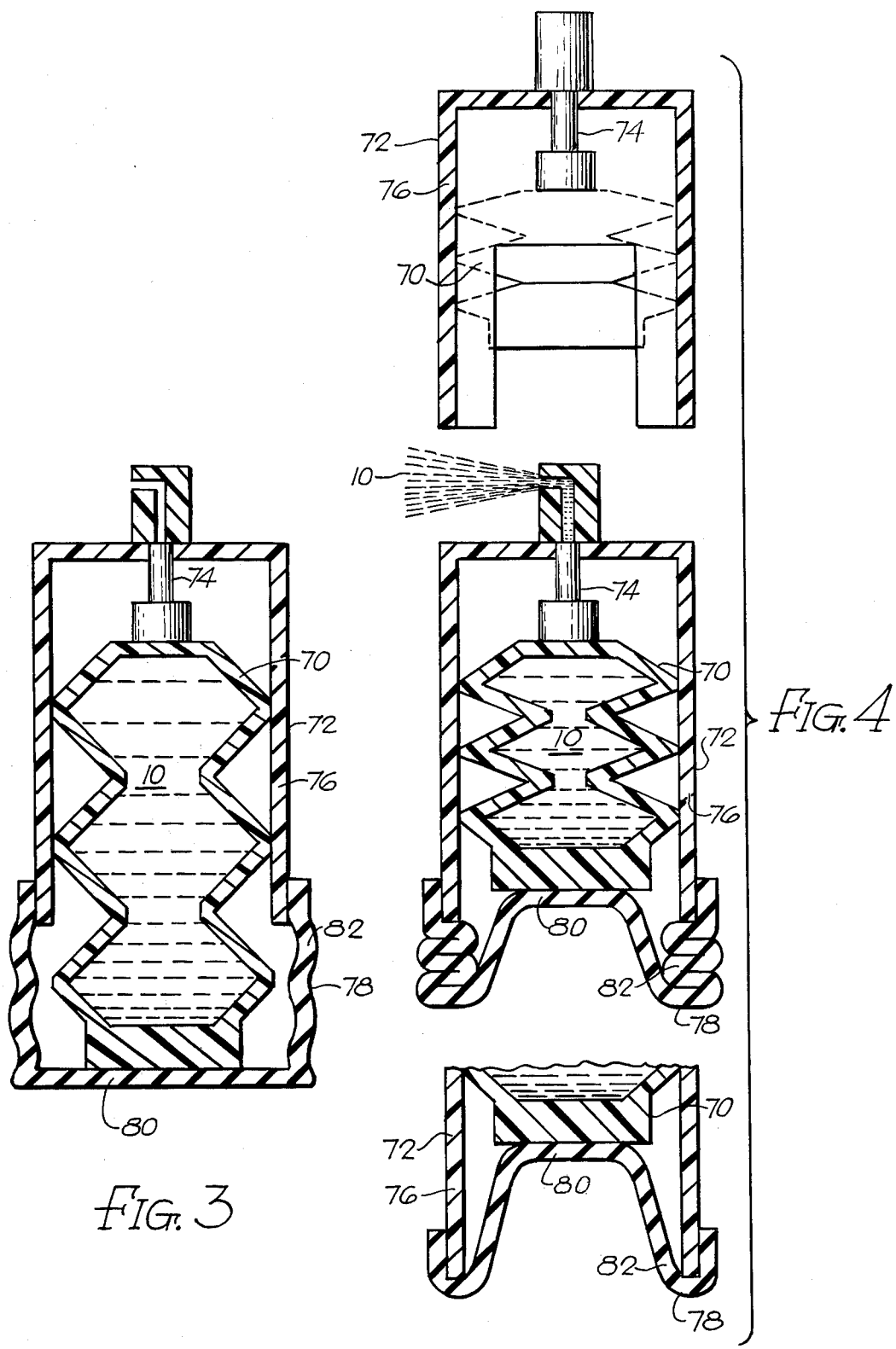
FIG. 3 is a sectional elevationsl view showing another embodiment of sprayer in the non-dispensing state.
FIG. 4 is a sectional view of a further modification of the sprayer 3 showing the relative position of elements when a substantial portion of the material has been dispensed.

FIGS. 3 and 4 show a modification of a device embodying the objectives heretofore described. Instead of loading the container itself with a liquid to be dispensed, the liquid 10 to be dispensed is packaged in a cartridge 70 of flexible material dimensioned to be received within the container 72 and provided with a nipple 74 at one end which is inserted into a passage for communication with the valve when the cartridge is inserted in position of use in the container.

In this modification, the container is subdivided longitudinally into two sections, including an upper section 76 of relatively rigid material and a lower section 78 having a rigid bottom wall 80 but foldable side walls 82, the upper ends of which are removably secured to the bottom edge portion of the side walls of the upper section 76 to define a completed container in which the cartridge 70 is received. In the illustrated modification, the side walls 82 are given a corrugated configuration for guiding the section in its folded relation in response to axial movement.

In use, the container is gripped in one hand with the thumb pressing on the bottom wall 80 and the fingers engaged over the top wall of the upper section 72. As the container is squeezed by the fingers, the bottom wall is urged for displacement upwardly in the direction toward the top wall and comes into pressing engagement with the cartridge 70 to pressurize the liquid content material for dispensing.

When the bottom wall 80 ultimately rises to the level of the lower end portion of the upper rigid section 72, only about half of the liquid content material has been dispensed from the cartridge. By reason of the resiliency of the side walls 82, supporting the bottom wall 80, it is now possible to continue the displacement of the bottom wall upwardly through the interior of the upper section, dragging the side walls 78 with it, as illustrated in FIG. 4. This enables substantially complete dispensing of the liquid content material from the cartridge. For this purpose, it is desirable to form the bottom wall 80 of a rigid and structurally strong material having a crosswise dimension which is less than the inner diameter of the upper section by an amount somewhat greater than twice the thickness of the side walls 82 thereby to enable the lower section to be drawn into the interior of the upper section with the bottom wall.

Instead of corrugating the side walls 82 of the lower section for guidance thereof in folding movement, the side walls of the lower section can be otherwise formed of a stretchable material, such as elastomeric material to enable movement of the bottom wall up to and through the upper section 72 of the container.

It will be apparent from the foregoing that there is provided a container from which liquid content material can be sprayed in continuous or intermittent fashion merely by operation with one hand to effect liquid content material to be sprayed without the need for foreign material to provide the dispensing pressure.

It will be understood that changes may be made in the details of construction, arrangement, and operation without departing from the spirit of the invention, especially as defined in the following claims.

I claim:

1. A non-aerosol spray device comprising a housing consisting of an upper rigid tubular section open at the bottom and closed at the top with a top wall having an outlet opening, and a lower corrugated tubular section formed of a flexible material open at the top and closed at the bottom in which the upper open end portion of the lower tubular section is fixed to the lower open end portion of the upper tubular section to define the housing therebetween, a collapsible cartridge containing fluid to be dispensed dimensioned to be received within the enclosure and having an outlet at the upper end in communication with the outlet opening, the bottom wall of the lower flexible section having a rigid portion dimensioned to be less in cross-section than the interior of the upper tubular section by an amount greater than twice the thickness of the wall of the lower section to enable displacement of the rigid portion of the bottom wall therethrough, said lower section being dimensioned to have a length corresponding to the length of the upper section to enable the rigid portion of the bottom wall to be displaced axially through the interior of the upper section for substantially complete collapsing of the cartridge and a spray nozzle fixed to the top wall of the upper tubular section in communication with the outlet opening.

2. A spray device as claimed in claim 1 in which the two sections of the container are separable for access to the interior for replacement of the cartridge.

* * * * *